(12) United States Patent
Lanin et al.

(10) Patent No.: US 8,597,256 B2
(45) Date of Patent: Dec. 3, 2013

(54) SEAL MEMBER

(75) Inventors: Irina Lanin, Frankfurt am Main (DE); Bernhard Forys, Frankfurt am Main (DE); Alastair Clarke, Cheshire (GB); Matthew Ekman, Cheshire (GB); Kirsten Goode, Cheshire (GB); Michael Heald, Berkshire (GB); John Hiles, Cheshire (GB); Chris Smith, Cheshire (GB); Andrew Martin, Bristol (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/202,439

(22) PCT Filed: Mar. 4, 2010

(86) PCT No.: PCT/EP2010/052789
§ 371 (c)(1),
(2), (4) Date: Jan. 6, 2012

(87) PCT Pub. No.: WO2010/100244
PCT Pub. Date: Sep. 10, 2010

(65) Prior Publication Data
US 2012/0095409 A1  Apr. 19, 2012

(30) Foreign Application Priority Data
Mar. 6, 2009 (EP) .................................... 09003278

(51) Int. Cl.
*A61M 5/24* (2006.01)
*A61M 5/28* (2006.01)
*A61M 5/20* (2006.01)
*A61M 5/315* (2006.01)

(52) U.S. Cl.
USPC ............ 604/200; 604/205; 604/157; 604/218

(58) Field of Classification Search
USPC ......... 604/156–157, 200–206, 218, 187–188, 604/195–196, 110
See application file for complete search history.

(56) References Cited

U.S. PATENT DOCUMENTS

| | | | |
|---|---|---|---|
| 2,735,429 A | 2/1956 | Huber | |
| 3,368,558 A | 2/1968 | Sarnoff et al. | |
| 3,735,761 A * | 5/1973 | Hurschman et al. | 604/88 |
| 5,601,534 A | 2/1997 | Turner | |
| 5,997,512 A | 12/1999 | Shaw | |
| 6,045,534 A | 4/2000 | Jacobsen et al. | |
| 6,796,969 B1 | 9/2004 | Andersson | |
| 2007/0276338 A1 * | 11/2007 | Shue et al. | 604/187 |

FOREIGN PATENT DOCUMENTS

WO 2009/003234 1/2009

OTHER PUBLICATIONS

European Search Report for EP Application No. 09003278, dated Jul. 22, 2009.
International Search Report and Written Opinion for Int. App. No. PCT/EP2010/052789, mailed Jun. 11, 2010.

* cited by examiner

*Primary Examiner* — Nicholas Lucchesi
*Assistant Examiner* — Rebecca E Eisenberg
(74) *Attorney, Agent, or Firm* — McDonnell Boehnen Hulbert & Berghoff LLP (57) ABSTRACT

A seal member is configured to seal a chamber of a drug delivery device which is suitable to contain a drug, wherein the seal member comprises a diaphragm.

16 Claims, 5 Drawing Sheets

SEAL MEMBER

CROSS REFERENCE TO RELATED APPLICATIONS

The present application is a U.S. National Phase Application pursuant to 35 U.S.C. §371 of International Application No. PCT/EP2010/052789 filed Mar. 4, 2010, which claims priority to EP Patent Application No. 09003278.0 filed on Mar. 6, 2009. The entire disclosure contents of these applications are herewith incorporated by reference into the present application.

FIELD OF INVENTION

The invention concerns a seal member configured to seal a chamber of a drug delivery device which is suitable to contain a drug.

BACKGROUND

WO 2009/003234 shows a pre-filled syringe having a retractable needle. In an initial state the proximal end of the needle extends through a seal to a chamber which contains the drug, so that the proximal end of the needle may be in contact with the drug before use of the syringe.

SUMMARY

It is an aim of the present invention to provide means suitable to prevent the contact between the needle and the drug before use.

For this purpose a seal member is provided, the seal member being configured to seal a chamber of a drug delivery device which is suitable to contain a drug, wherein the seal member comprises a diaphragm.

The diaphragm which comprises a flexible membrane seal and isolates the chamber of the drug delivery device and provides a fluid seal so that leakage of fluid contents out of the chamber is prevented. The diaphragm is flexible and this allows the chamber contents to change volume in response to pressure differences across the membrane while preventing fluid content of the chamber from crossing the membrane. The diaphragm material is resilient and resistant to tearing and may comprise a laminate of different materials to provide the correct collection of properties.

A drug delivery device is configured to expel a drug. One embodiment of the drug delivery device is configured to inject the drug by a needle. The drug delivery device may be designed as e.g. an auto-injector, injection drug delivery device, pen-type drug delivery device or syringe.

In one embodiment the chamber is located inside a body of the drug delivery device, which may be pre-filled, e.g. designed as a pre-filled syringe. The chamber may be defined by the seal member which forms the distal wall of the chamber, the inside walls of a syringe barrel which form the side walls and a bung which forms the proximal wall. In one embodiment the chamber is designed as a cartridge of a drug delivery device. The cartridge may be a removable part of the drug delivery device.

In one embodiment the seal member comprises a periphery which is configured to engage with an opening of the chamber and a flexible membrane which covers the opening. The opening of the chamber is engaged with the periphery of the seal member so that the seal member provides a fluid seal which means that leakage of fluid content from the chamber is prevented. In one embodiment the seal member forms a wall of the drug-containing chamber. In one embodiment, the periphery is engaged by means of mechanical friction, e.g. a rubber seal member is frictionally connected inside a barrel of a syringe. In one embodiment the periphery is engaged by engagement means, e.g. the periphery is mounted by a circumferential rib on an inside wall of a housing of the drug delivery device.

The membrane allows pressure effects, but not the drug, to cross the barrier formed by the seal member. In other words, the membrane is deformable, e.g. by hydrostatic pressure.

In one embodiment the seal member is made of one piece, in particular of the same material, e.g. rubber or plastic. In an alternative embodiment the periphery and the membrane are mounted.

One embodiment of the drug delivery device further comprises a needle assembly having a needle with distal and proximal ends. The drug can be expelled through the needle.

In one embodiment the seal member serves as a barrier between the needle and the chamber. The seal member separates the drug inside the chamber and the proximal end of the needle so that the needle does not contact the drug inside the chamber. This arrangement prevents contact between the needle and the drug before use. One advantage is that the liquid if previously sterilised remains sterile. Another advantage is that drug stability is improved because reaction with the needle is not possible.

A conventional pre-filled safety syringe has a retractable needle. The proximal end of the retractable needle is coated or has its shape changed (by metal form techniques such as pressing) by e.g. plastic so that a needle mount is formed, the needle mount being suitable to be engaged with retracting means during retraction of the needle after drug delivery. The syringe has a needle seal forming the distal wall of the chamber which contains the drug wherein a retractable needle extends through the needle seal so that the proximal end of the needle may be in contact with the drug. In a conventional syringe, it is necessary that the proximal tip of the needle is not coated. If the coating and the drug would interact, the drug stability characteristics may decrease. Therefore, the coating located at the very proximal end of the needle must be removed during manufacturing of the conventional drug delivery device.

The needle of the inventive drug delivery device may have a coating located at the very proximal end of the needle. This coating does not influence the drug stability characteristics because the needle and the drug are not in contact before use. Thus, the manufacturing process is simplified because the coating located at the very proximal end of the needle has not to be removed.

One embodiment of the drug delivery device comprises compression means configured to compress the chamber thereby deforming the membrane so that the center of the membrane moves towards the proximal end of the needle. The proximal end of the needle is configured to puncture the membrane. The membrane is punctured by the needle when hydrostatic pressure due to deformation of the chamber deforms the membrane so that it is pushed towards the needle. The drug can then be expelled through the needle. The needle may be formed so that when the pressure or bung is reversed the membrane remains attached to the needle. Alternatively the needle end may be shaped so that the membrane slips off the needle closing to keep the fluid contained.

In one embodiment the chamber has side walls. The compression means are formed as a bung which is located at the proximal end of the chamber, the bung being movable along side walls of the chamber towards the seal member. In other words, the chamber is compressed when the bung moves to the distal direction with respect to the side walls of the chamber, which may be formed by a barrel of a syringe. Thereby, hydrostatic pressure impacts to the membrane.

One embodiment of the drug delivery device has a needle assembly comprising a needle retainer which is configured to secure the needle against displacement with respect to the needle retainer and an ejector member being configured to interact with the needle retainer so that the needle is unlocked.

The needle retainer secures the releasable needle against displacement with respect to the needle retainer during drug delivery. The ejector member is suitable to unlock the needle when the drug has been delivered. In one embodiment the needle is unlocked, when the center of the membrane moves towards the needle retainer.

One embodiment comprises an ejector member which is configured to interact with the needle retainer so that the needle is unlocked. In one embodiment the ejector member unlocks the needle when the ejector member is pushed towards the needle retainer.

In one embodiment the center of the membrane is movable towards the ejector member so that the ejector member interacts with the needle retainer. In one embodiment the ejector member is pushed towards the needle retainer when the membrane moves towards the ejector member. In one embodiment the membrane is moved towards the ejector member when the bung reaches the membrane. The periphery of the seal member does not move to the distal direction when the membrane is pushed towards the ejector member. Unlocking the needle by pushing only the membrane towards the ejector member requires less pressure in comparison with a conventional device wherein the whole seal is moved towards the ejector member to unlock the needle.

In an alternative embodiment of the drug delivery device, the needle assembly comprises a needle holder which is mounted to the needle. The needle holder is movable in the distal direction with respect to a housing of the drug delivery device so that the needle moves from a first position, where the needle is positioned inside the housing, to a second position, where the needle is extended from the housing. If the drug delivery device is a syringe the housing may be a barrel of the syringe. This embodiment has a needle which extends when the drug delivery device is used. This arrangement prevents needle sticking injuries before use of the drug delivery device.

In one embodiment the seal member is configured to move in the distal direction with respect to the housing from a first position to a second position when the bung is moved in the distal direction with respect to the housing. The pressure caused by the movement of the bung pushes the seal member distally, thereby the seal member pushing the needle holder in the distal direction so that the needle extends.

In one embodiment the needle punctures the membrane when the seal member engages with the needle holder. After puncturing the drug is expelled through the needle. This embodiment may have a retractable needle. When the needle is refracted into the housing, the seal member is moved in the proximal direction with respect to the housing due to the coupling of the seal member and the needle holder.

One embodiment of the drug delivery device comprises refraction means which are configured to retract the needle to the proximal direction with respect to the needle retainer. The retraction means are suitable to retract the needle into the drug delivery device when the needle is unlocked. One embodiment of the retraction means automatically retracts the needle into the drug delivery device when the drug has been delivered. Retraction may be performed by means of a compressed spring which decompresses in order to retract the needle.

One embodiment of the drug delivery device comprises engagement means configured to engage with the needle assembly. The needle assembly is engaged with the engagement means so that the needle is retractable after engagement.

In one embodiment, the bung is retractable to the proximal direction with respect to the needle retainer. The bung comprises the engagement means. When the bung is retracted the needle which is engaged with the bung is also refracted. One embodiment of the engagement means is formed as a cavity. One embodiment of the engagement means is formed as a snapping means.

In one embodiment, the needle comprises mating means configured to engage with the engagement means. The mating means may be formed as a needle mount located at the proximal end of the needle. The needle mount fits into the cavity of the bung so that the needle is retracted by the bung when the bung moves to the proximal direction with respect to the needle retainer. This has the advantage that the remaining volume of drug in the drug container is small.

In another embodiment the drug delivery device comprises a medicament. The medicament could be pre-filled in a cartridge or, if the drug delivery device is designed as a syringe, pre-filled in the syringe.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-

N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane such as hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Other features will become apparent from the following detailed description when considered in conjunction with the accompanying drawings.

DETAILED DESCRIPTION

Figure 1:
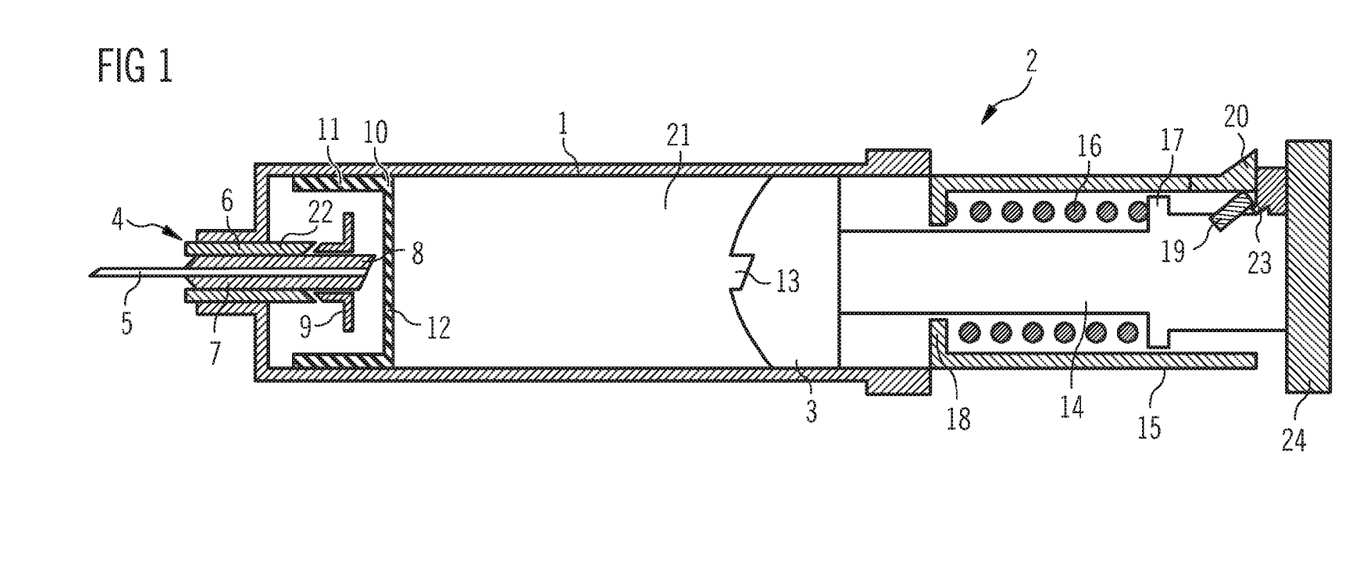
FIG. 1 shows a sectional view of an embodiment of a pre-filled syringe.

Referring to FIG. 1, a sectional view of an embodiment of a pre-filled syringe is shown, the syringe containing drug. The drawing is not to scale for clarity reasons.

The syringe comprises a barrel 1 having distal and proximal ends and a plunger 2 having distal and proximal ends.

One embodiment of the barrel 1 is made of glass. An alternative embodiment of the barrel 1 is made of plastic. The distal end of the plunger 2 is located inside the barrel 1. The plunger 2 comprises a bung 3 located at the distal end of the plunger 2. The bung 3 moves to the distal direction with respect to the barrel 1 when the plunger 2 moves to the distal direction with respect to the barrel 1.

A needle assembly 4 is located at the distal end of the barrel 1. The needle assembly 4 comprises a needle 5 and a needle retainer 6 which is mounted inside the distal end of the barrel 1. The needle 5 comprises a needle coating 7 which covers the proximal part of the needle 5. The needle coating 7 has a rough-textured surface. In one embodiment the coating 7 is made of plastic. An alternative embodiment has a shape pressed or formed into the needle. The proximal end of the needle 5, which is coated by the needle coating 7, is formed as needle mount 8 having a sharp tip.

In one embodiment the barrel 1 and the needle retainer 6 are integrally formed. The needle retainer 6 is configured to secure the needle 5 against displacement with respect to the needle retainer 6. This embodiment of the needle retainer 6 comprises a cylindrical body and fingers 22 extending to the distal direction. The needle retainer 6 has an aperture through which the needle 5 extends. The fingers 22 abut the needle coating 7 to releasably hold the needle 5 in position during provision and use of the syringe. The needle 5 is unlocked when the fingers 22 are forced apart or bent away from the needle 5.

In one embodiment the needle 5 is releasably engaged with the needle retainer 6 by a friction-locking joint between the needle retainer 6, in particular the fingers 22 of the needle retainer, and the rough-textured surface of the needle coating 7. In one embodiment the needle 5 is releasably engaged with the needle retainer 6, in particular the fingers 22 of the needle retainer, by a positive locking, e.g. by snapping means.

An ejector member 9 is provided in the needle assembly 4, the ejector member 9 being configured to interact with the needle retainer 6 so that the needle 5 is unlocked. The ejector member 9 has an aperture which the needle 5 extends through. The ejector member 9 furthermore comprises an ejector ring which is oriented towards the needle retainer 6 and a base which is averted from the needle retainer 6. In one embodiment the ejector member 9 is not fixed or positively mounted or engaged with needle coating 7. In one embodiment (not shown) ejector member 9 is releasably fixed with needle coating 7, e.g. the ejector member engaging a circumferential recess on needle coating via an annular detent.

The ejector member 9 is movable to the distal direction with respect to the needle retainer 6 so that the ejector ring moves towards the fingers 22 of the needle retainer in order to bend them radially outwards when the base of the ejector member 9 is pushed. For this purpose the tips of the fingers 22 of the needle retainer and the distal end of the ejector ring may be sloped in order to facilitate forcing apart the fingers 22 of the needle retainer by means of the ejector member 9.

A seal member 10 is provided which comprises a periphery 11 and a center area which is formed as flexible membrane 12. The seal member 10 serves as a diaphragm seal. The flexibility of the membrane 12 allows pressure effects, but not the drug, to cross the barrier formed by the seal member 10.

The seal member 10 is located between the bung 3 and the needle assembly 4 so that the proximal end of the needle 5 does not touch the membrane 12 in an initial state before the syringe is used. In one embodiment, the ejector member 9 is not fixed or positively mounted or engaged with seal member 10.

A fluid content, i.e. the drug, is contained in a chamber 21 formed by the barrel 1 which forms the side walls of the chamber 21, the bung 3 which forms the proximal wall of the chamber 21 and the seal member 10 which forms the distal wall of the chamber 21. The bung 3 co-operates with an inside wall of the barrel 1 to provide a fluid seal so that leakage of fluid contents is prevented.

The periphery 11 co-operates with an inside wall of the barrel 1 to provide a fluid seal so that leakage of fluid contents of the chamber 21 is prevented. The seal member 10 seals the chamber 21 containing the drug. If the drug inside the chamber 21 is compressed the membrane 12 is deformed so that the center of the membrane 12 moves to the distal direction with respect to the periphery 11, which cause puncturing of the membrane 12 by the proximal end of the needle 5.

The plunger 2 is provided in an initial position before use, ready for depression to deliver the fluid content of the syringe if the syringe is pre-filled with the drug for delivery.

In use, the plunger 2 is movable into the distal direction with respect to the barrel 1 to facilitate delivery of the drug of the syringe.

The plunger 2 comprises an engaging means configured to engage with the needle 5 when the drug is delivered. The engaging means is designed as cavity 13 located at the distal side of the bung 3. The cavity matches with the proximal end of the needle 3 designed as needle mount 8. The cavity 13 engages with the needle mount 8 when the bung 3 is pushed towards the proximal end of the needle 5 after drug delivery.

Moreover, when the drug is delivered, the bung 3 further pushes the membrane 12 towards the distal direction, so that the membrane moves the ejector member 9 towards the needle retainer 6. The ejector member 9 interacts with the needle retainer 6 in order to unlock the needle 5.

The plunger comprises a plunger rod 14 and a plunger housing 15. The plunger 2 further comprises a compressed spring 16 which is mounted between the plunger rod 14 and the plunger housing 15. The spring 16 is held in a compressed state between an annular ledge 17 of the plunger rod and a base of 18 the plunger housing.

The plunger rod 14 comprises a first arm 19 extending radially outwards. The first arm 19 can be bent inwards. In the initial position the first arm 19 is engaged with a pawl 23 of the plunger housing. This engagement prevents a proximal movement of the piston rod 14 with respect to the piston housing 15.

The piston housing 15 comprises a second arm 20 having a protrusion. The second arm 20 is configured to push the first arm 19 inwards when the second arm is bent inwards. When the first arm 19 is bent inwards the first arm 19 is no longer engaged with the pawl 23 so that the piston rod 14 is movable to the proximal direction with respect to the piston housing 15.

The proximal part of the plunger rod 14 is designed as button 24, which the user can press in order to expel the drug. The piston 2 moves to the distal direction with respect to barrel 1 when the user presses the button 24.

The compressed spring 16 must decompress in order to retract the needle 5 after unlocking it. Retraction is facilitated by the plunger rod 14 disengaging from the plunger housing 15. The axial movement of the plunger 2 in the distal direction brings the protrusion of the second arm 20 to bear against the proximal end of the barrel 1 when the drug has been dispensed. In one embodiment (not shown), the plunger housing 15 engages which the barrel 1 when the proximal end of the plunger housing 15 reaches the barrel 1. When the protrusion of the second arm 20 is pushed towards the proximal end of the barrel 1 the second arm 20 is bent inwards which forces first arm 19 to move out of engagement with the pawl 23. This disengagement allows compressed spring 16 to decompress and push against the ledge 17 of the plunger rod to thereby retract the plunger rod 14. The retractable needle 5 is coupled to the bung 3 so the needle can be retracted with the plunger rod 14 in the distal direction with respect to the barrel 1.

In an alternative embodiment (not shown) the needle is retracted by manually pulling the piston 2 in the proximal direction with respect to barrel 1 after drug delivery.

FIGS. 2 to 5 show detailed sectional views of the distal part of the syringe. Steps of delivering the drug and then retracting the needle are shown.

Figure 2:
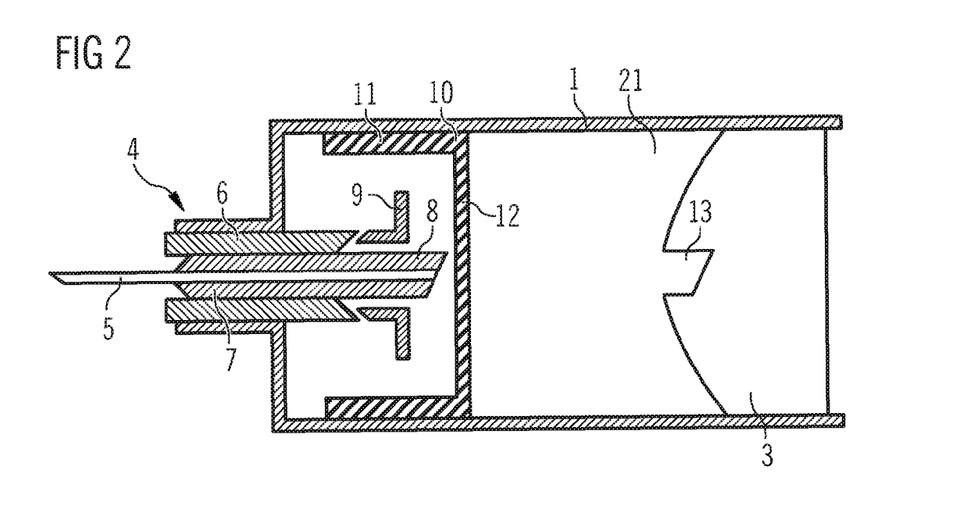
FIG. 2 shows a detailed sectional view of a part of the syringe in an initial position.

FIG. 2 shows a detailed sectional view of the distal part of the syringe in the initial position. The drawing is not to scale for clarity reasons.

The bung 3 is located in the initial position ready for depression to deliver the drug which is contained in the syringe.

The needle assembly 4 comprises the needle 5 which is secured against displacement by the needle retainer 6. The seal member 10 is frictionally located inside the barrel 1 of the drug delivery device, positioned such that the drug is isolated from the needle 5. The periphery 11 of the seal member is frictionally connected with the inside wall of the barrel 1. In one embodiment frictional connection is achieved if the diameter of the periphery 11 is, e.g. slightly, larger than the inside diameter of the barrel 1.

In this embodiment the periphery 11 and the membrane 12 of the seal member 10 are integrally formed. The thickness of the tube-shaped periphery 11 is larger than the thickness of the flexible membrane 12. The thickness of the periphery 11 ensures that the seal member 10 facilitates sealing performance and prevents inadvertent leakage of the fluid content. In one embodiment (not shown) the periphery 11 has annular ribs cooperating with the inside wall of the barrel 1 to increase sealing performance.

The flexible membrane 12 allows pressure effects, but not the drug, to cross the membrane 12. In other words, the membrane 12 is deformed when pressure impacts to the membrane 12.

The needle 5 is at least partly coated to form a needle mount 8 located at the proximal end of the needle 5. In one embodiment, the proximal end of the needle 5 is close to, but not touching, the membrane 12.

Removing the needle material and/or the coating material from contact with the drug before using the syringe improves drug stability characteristics. The membrane 12 separates the drug content and the needle coating 7, which prevent chemical interaction between the material of needle coating 7 and the drug inside the syringe.

Figure 3:
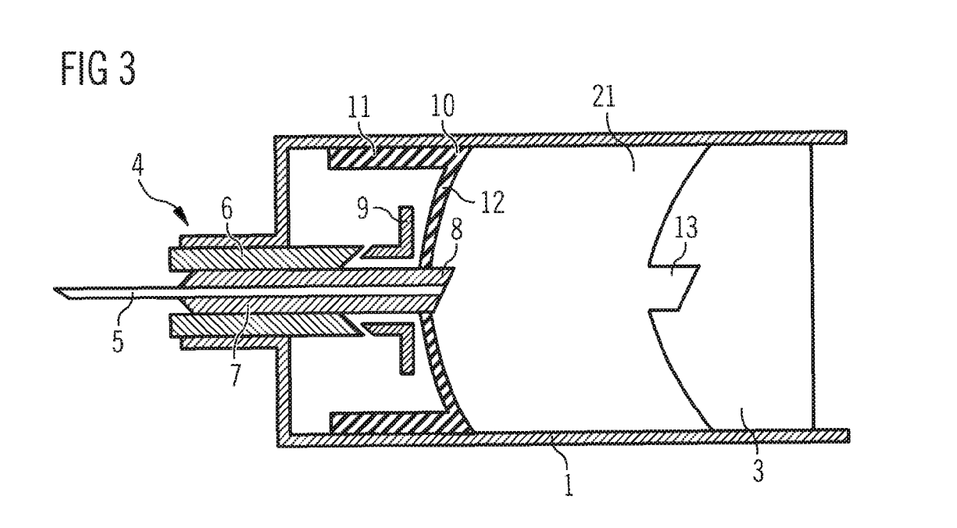
FIG. 3 shows a detailed sectional view of a part of the syringe as the drug delivery begins.

FIG. 3 shows a detailed sectional view of the distal part of the syringe as the drug delivery begins.

The piston 2 (not shown) is pushed in the distal direction with respect to the barrel 1. Thereby, the bung 3 starts to move along the barrel 1 in the distal direction. The chamber 21 which contains the drug is compressed so that the hydrostatic pressure which results from the distally moving bung 3 deforms the flexible membrane 12 concavely. A center area of the membrane 12 moves towards the proximal end of the needle 5. The periphery 11 of the seal member is fixed.

The drug contacts the needle 5 for the first time at the beginning of the delivery process. The seal member 10 and the needle 5 are positioned so that the sharpened proximal tip of the needle 5 punctures the membrane 12 when the bung 3 starts to move along the barrel 1 during drug delivery so that the center of the membrane 12 is moved in the distal direction. Puncturing allows the drug to enter the needle 5 and be expelled from the drug delivery device.

The membrane 12 is deformed such that the needle 5 punctures through the membrane 12 when the hydrostatic pressure is impacting the seal member 10 during the delivery process. If the distal movement of the bung 3 stops, the drug would be expelled until the membrane 12 is removed from the needle 5 thereby separating the needle 5 and the drug containing chamber 21.

However, this embodiment shows a pre-filled syringe containing a dose of the drug which is delivered in one go. Typically, the bung 3 moves in the distal direction until the drug is completely expelled.

Figure 4:
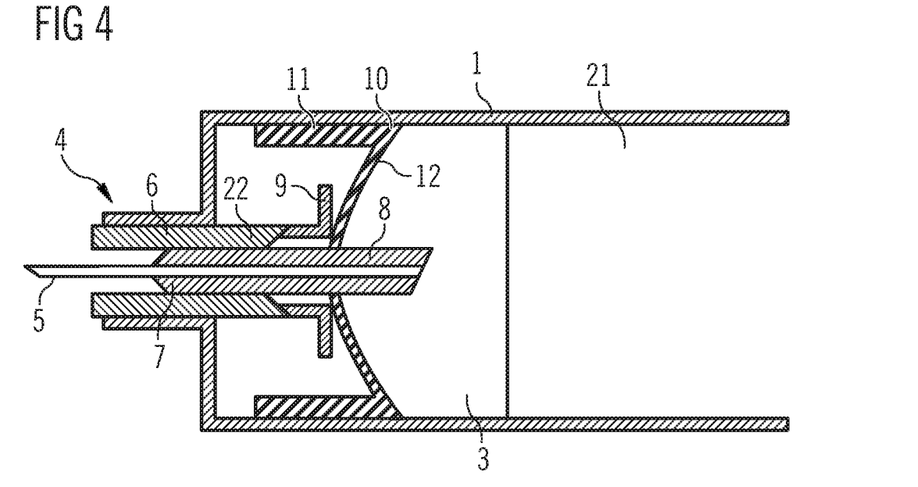
FIG. 4 shows a detailed sectional view of a part of the syringe as the drug has been delivered.

FIG. 4 shows a detailed sectional view of the distal part of the syringe when the drug has been delivered.

During drug delivery the bung 3 is moved from the initial position towards the seal member 10. When the drug is expelled the bung 3 comes in contact with the seal member 10. When the bung 3 further moves in the distal direction the cavity 13 located in the bung 3 receives the needle mount 8 of the needle, the needle mount 8 being inserted into the cavity 13. This movement effectively couples the retractable needle 5 with the bung 3. The needle mount 8 and the cavity 13 are coupled mechanically by friction. In one embodiment (not shown) the needle and the bung are coupled by snapping means.

The distal surface of the bung 3 is configured to push the membrane 11 of the seal member so that the ejector member 9 interacts with the needle retainer 6 in order to unlock the needle 5 from the needle retainer 6. In one embodiment the periphery 11 of the seal member does not move with respect to barrel 1, but the membrane 12 is deformed when the bung 3 further moves towards the seal member 10 when the drug is delivered.

When the bung 3 reaches the seal member 10 the membrane 10 may be deformed by the bung 3. In one embodiment, the bung 3 is suitable to cause a deformation so that the center area of the membrane 12 is moved further in the distal direction in comparison with the deformation caused by the hydrostatic pressure. The ejector member 9 is pushed towards the needle retainer so that the fingers 22 of the needle retainer are forced apart. Thereby, the needle 5 is unlocked.

In this embodiment the distal surface of the bung 3 is formed convexly as a dome. In one embodiment (not shown) the distal surface of the bung has an alternative form which is suitable to cause a deformation of the membrane 12 which is sufficient to push to the ejector member 9 towards the needle retainer 6.

Figure 5:
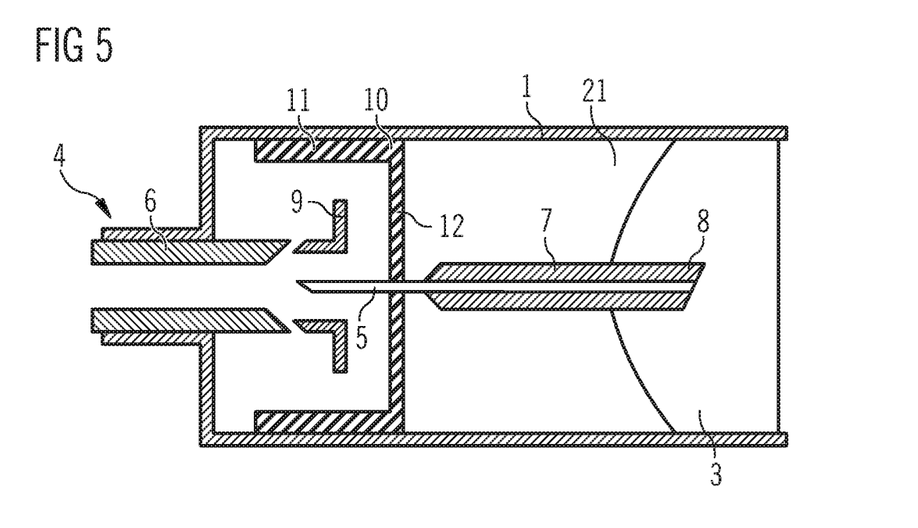
FIG. 5 shows a detailed sectional view of a part of the syringe wherein the needle is withdrawn.

FIG. 5 shows a detailed sectional view of the distal part of the syringe wherein the needle is withdrawn.

If the needle mount 8 is engaged with the cavity 13 of the bung the needle 5 could be retracted into the barrel 1. When the bung 3 is removed in the proximal direction the needle is at least partly withdrawn through the membrane 12 of the seal member 10 located inside the barrel 1. The seal member 10 remains in place.

Retraction may be achieved by retraction means as described above exemplary, wherein the plunger rod is decoupled from the plunger housing, or by manually retracting the plunger of the drug delivery.

The retraction of the needle prevents needle stick injuries and allows safe disposal of the syringe.

In one embodiment (not shown) the drug delivery device has a seal member which is located so that the proximal end of the needle punctures the membrane in the initial state if the drug delivery device is provided. Thus, the needle may then come into contact with the drug in the drug-containing chamber. One embodiment (not shown) of the drug delivery device is designed like the embodiment shown in FIG. 1, but the proximal end of the needle punctures the seal member in the initial state.

When the drug is delivered the bung is moved towards the membrane so that the membrane is pushed towards the ejector member, thereby the ejector member interacts with the needle retainer so that the needle is unlocked. Thereby allowing the needle to be retracted inside the body of the delivery device.

An additional implementation could be configured so that the needle is placed within barrel 1 and by hydraulic pressure is moved forwards out of the syringe body and into the receiving patient. The retraction means can then act on the whole of the needle assembly or just the proximal end.

Figure 6A:
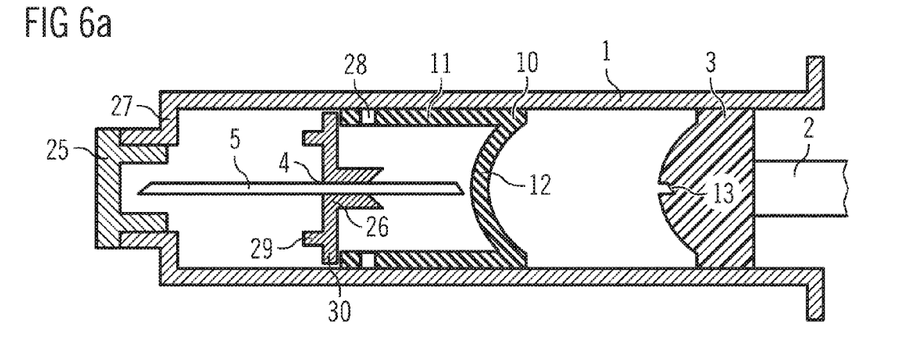
FIG. 6a shows a detailed sectional view of the distal part of another embodiment of a syringe in the initial position.

FIGS. 6a, b 6, 6c, 7 and 8 show detailed sectional views of the distal part of a further embodiment of a syringe. Steps of delivering the drug and then retracting the needle are shown.

FIG. 6a shows a detailed sectional view of the distal part of the syringe in the initial position. The drawing is not to scale for clarity reasons.

The syringe comprises a barrel 1 having a distal end and a proximal end. A bung 3 is located at a proximal end of the barrel 1. The bung 3 is located in the initial position ready for depression to deliver the drug which is contained in the syringe. The distal end of the barrel 1 has an aperture which is covered by a needle cover 25. One embodiment of the needle cover 25 covers the aperture so that the inside of the barrel 1 if sterilised remains sterile.

The needle assembly 4 comprises a needle holder 26 which is mounted to a needle 5. The distal end and the proximal end of the needle 5 are sharpened. In one embodiment a needle mount is provided. In the initial position the needle holder 26 and the needle 5 are located inside the barrel 1 so that the distal tip of the needle 5 neither touches nor punctures the needle cover 25. The needle holder 26 is configured to move along the inside wall of the barrel 1. The needle holder has a center part holding the needle 5 and an outer part 30 which is located adjacent to the inside wall of the barrel 1. In one embodiment at least a part of the outer part 30 touches the inside wall of the barrel 1. One embodiment of the needle holder 26 is embodied as plate having a hole the needle 5 extends through. One embodiment of the needle holder 26 comprises a ring which is suitable to hold the needle 5 and fingers which radially extend from the ring to or nearly to the side wall of the barrel 1. In one embodiment the needle 1 is hold by a sleeve or barrel located at the center of the needle holder 26.

A spacing means 29 is located at the distal side of the needle holder 28. In one embodiment the spacing means 29 is designed as a ring. In an alternative embodiment the spacing means 29 is designed as a plurality of protrusions.

The needle holder 26 is movable along the inside wall of the barrel 1. The needle holder 26 is movable in the distal direction with respect to the barrel 1 until the spacing means 29 of the needle holder reaches a distal ledge 27 of the barrel. The needle 5 does not move with respect to the needle holder 26, but when the needle holder 26 is moved in the distal direction the needle 5 moves along a longitudinal axis in the distal direction. When the needle holder 26 is moved in the proximal direction the needle 5 moves along the longitudinal axis in the proximal direction.

A seal member 10 having a periphery 11 and a membrane 12 is located inside the barrel 1 of the drug delivery device, positioned such that the drug is isolated from the needle 5.

The flexible membrane 12 allows pressure effects, but not the drug, to cross the membrane 12. In this embodiment the membrane 12 is concavely shaped in the initial position. In one embodiment the material of the membrane is pre-shaped. In an alternative embodiment the drug is provided in the drug-containing chamber in a pressurized manner so that the membrane is deformed in the initial position. In the initial position the proximal end of the needle 5 does not touch the membrane 12.

The periphery 11 of the seal member is frictionally connected with the inside wall of the barrel 1. The periphery 11 comprises engaging means 28 which are configured to engage with the needle holder 26, in particular the outer part 30 of the needle holder. In one embodiment the engaging means 28 is formed as circumferential trench located at the distal part of the inner wall of a tube-shaped periphery 11. The trench interferes with the outer edge of the plate of a needle holder 26 or with the finger tips of another embodiment of the needle holder 26. In one embodiment the engaging means 28 is formed as a plurality of holes which are arranged so that the finger tips of the needle holder can interfere with the holes in the periphery 11. However, in the initial position the periphery 11 and the needle holder 26 are not connected.

Figure 6B:
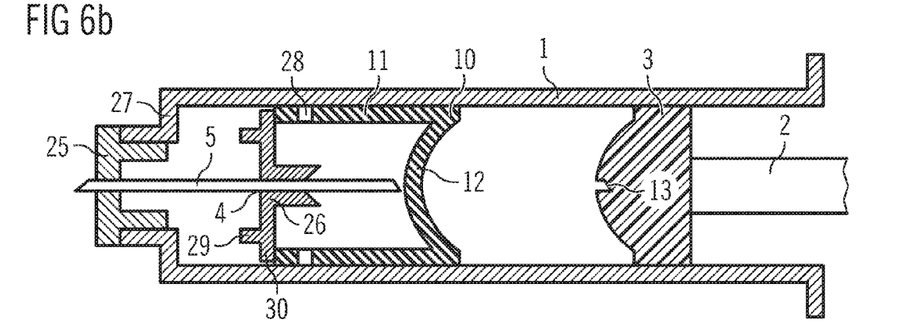
FIG. 6b shows a detailed sectional view of the distal part of the syringe in a piercing start position.

FIG. 6b shows a detailed sectional view of the distal part of the syringe in a piercing start position.

The piston 2 (partly shown) is pushed in the distal direction with respect to the barrel 1. Thereby, the bung 3 starts to move along the barrel 1 in the distal direction. The chamber 21 which contains the drug is compressed so that the hydrostatic pressure which results from the distally moving bung 3 pushes the seal member 10 to the distal direction with respect to the barrel 1. The shaped membrane 12 and the periphery 11 move distally.

When the bung 3 is moved in the distal direction with respect to the barrel 1 the distal end of the periphery 11 pushes the needle holder 26 in the distal direction with respect to the barrel 1, so that the distal tip of the needle 5 punctures the needle cover 25. The needle 5 extends through the needle cover 25 on further distally movement of the needle holder 26.

The needle holder 26 moves distally with respect to the barrel 1 until the spacing means 29 reaches the distal ledge 27 of the barrel.

Figure 6C:
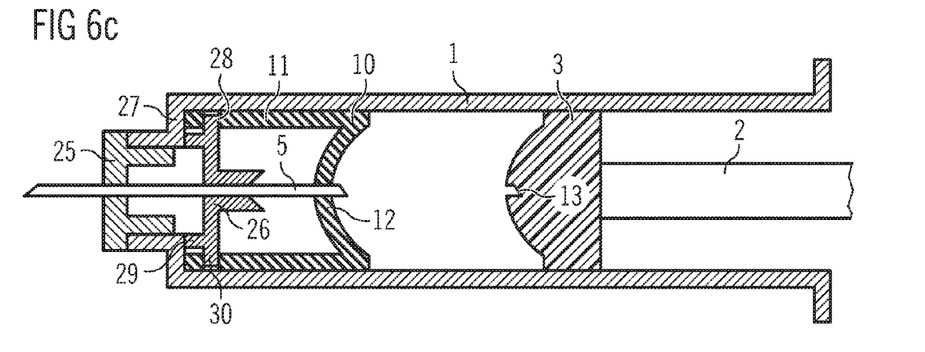
FIG. 6c shows a detailed sectional view of the distal part of the syringe in a drug injection starting position.

FIG. 6c shows a detailed sectional view of the distal part of the syringe in a drug injection starting position.

The bung 3 is further moved in the distal direction when the spacing means 29 reaches the distal ledge 27 of the barrel 1. Hydrostatic pressure impacts to the seal member 10 due to the further movement so that the distal edge of the periphery 11 is further pushed towards the outer part of the needle holder. The engaging means 28 of the periphery engages with the outer part 30 of the needle holder. In one embodiment the periphery 11 which is made of a flexible material is deformed so that the outer part 30 of the needle holder slides over the distal part of the inner wall of the periphery into the engaging means 28. In one embodiment the distal end of the periphery 11 is pushed towards the distal ledge 27 of the barrel so that the finger tips of the needle holder 26 are inserted to the trench-formed engaging means 28.

When the engaging means 28 and the outer part 30 of the needle holder are connected, the proximal end of the needle 5 punctures the membrane 12.

The seal member 10 and the needle 5 are positioned so that the sharpened proximal end of the needle 5 punctures the membrane 12 when the engaging means 28 and the outer part 30 of the needle holder are connected. Puncturing allows the drug to enter the needle 5 and be expelled from the drug delivery device.

This embodiment shows a pre-filled syringe containing a dose of the drug which is delivered in one go. The bung 3 moves in the distal direction until the drug is completely expelled.

Figure 7:
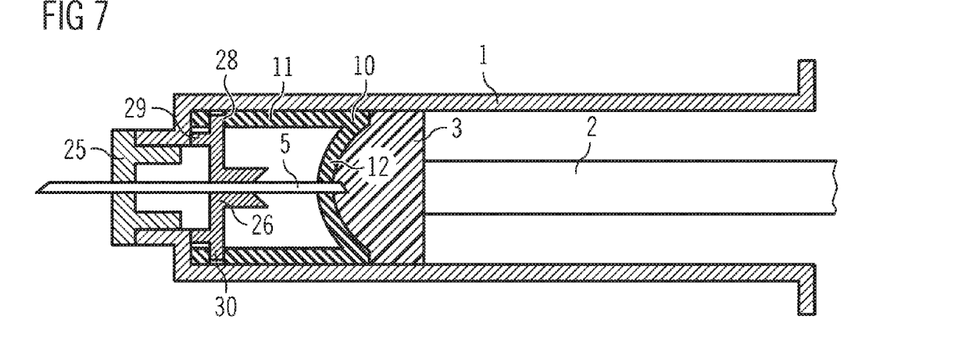
FIG. 7 shows a detailed sectional view of the distal part of the syringe when the drug has been delivered.

FIG. 7 shows a detailed sectional view of the distal part of the syringe when the drug has been delivered.

During drug delivery the bung 3 is moved towards the seal member 10. When the drug is expelled the bung 3 comes in contact with the seal member 10. When the bung 3 further moves in the distal direction a cavity 13 located in the bung 3 receives the needle mount (not explicitly shown) of the needle 5, the needle mount being inserted into the cavity 13. This movement effectively couples the retractable needle 5 with the bung 3. The needle mount 8 and the cavity 13 are coupled mechanically by friction. In one embodiment (not shown) the needle and the bung are coupled by snapping means.

When the bung 3 reaches the seal member 10 the membrane 10 may be deformed by the bung 3. In one embodiment, the bung 3 is suitable to cause a deformation so that the center area of the membrane 12 is moved further in the distal direction. In this embodiment the distal surface of the bung 3 is formed convexly as a dome.

Figure 8:
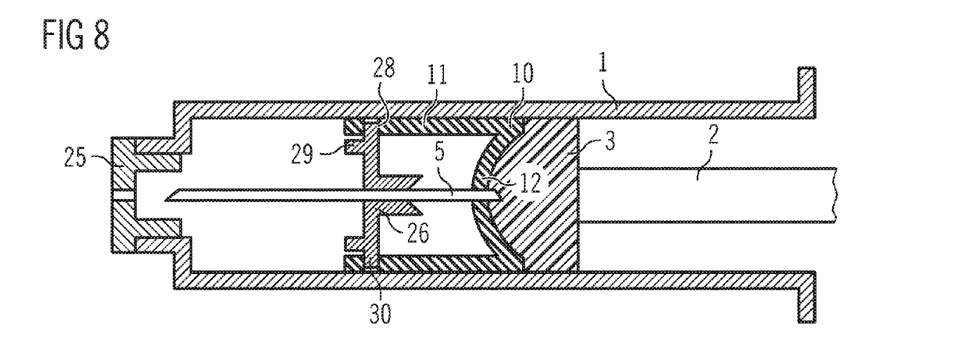
FIG. 8 shows a detailed sectional view of the distal part of the syringe wherein the needle is withdrawn.

FIG. 8 shows a detailed sectional view of the distal part of the syringe wherein the needle is withdrawn.

If the needle mount 8 is engaged with the cavity 13 of the bung the needle 5 could be retracted into the barrel 1. The needle holder 2 which is coupled to the seal member 10 is mounted to the needle 5 so that the needle holder 26 and the seal member 10 move proximally when the needle 5 is being retracted.

When the bung 3 is removed in the proximal direction the needle is at withdrawn through the needle cover 25, which remains in place.

Retraction may be achieved by retraction means as described above exemplary, wherein the plunger rod is decoupled from the plunger housing, or by manually retracting the plunger of the drug delivery.

The retraction of the needle prevents needle stick injuries and allows safe disposal of the syringe.

Other implementations are within the scope of the claims. Elements of different embodiments may be combined to form implementations not specifically described herein.

The invention claimed is:

1. A drug delivery device comprising a seal member being configured to seal a chamber of a drug delivery device which is suitable to contain a drug, wherein the seal member comprises a diaphragm comprising a deformable membrane, and comprising a needle assembly having a needle with a distal end and a proximal end, wherein the needle assembly further comprises a needle retainer which is configured to secure the needle against displacement with respect to the needle retainer, and wherein the needle is unlocked when the deformable membrane moves towards the needle retainer.

2. The drug delivery device according to claim 1 wherein the seal member further comprises a periphery which is configured to engage with an opening of the chamber.

3. The drug delivery device according to claim 1, wherein the seal member is made of one piece.

4. A drug delivery device according to claim 1, wherein the seal member serves as a barrier between the needle and the chamber.

5. A drug delivery device according to claim 4, comprising compression means to compress the chamber thereby deforming the deformable membrane so that at least the centre of the deformable membrane moves towards the proximal end of the needle.

6. A drug delivery device according to claim 5, wherein the proximal end of the needle is configured to puncture the deformable membrane.

7. A drug delivery device according to claim 5, wherein the chamber has side walls, and wherein the compression means is formed as a bung located at the proximal end of the chamber, the bung being moveable along side walls of the chamber towards the seal member.

8. A drug delivery device according to claim 1, comprising an ejector member which is configured to interact with the needle retainer in order to unlock the needle, wherein the deformable membrane is moveable towards the ejector member so that the ejector member interacts with the needle retainer.

9. A drug delivery device according to claim 1, comprising retraction means which are configured to move the needle in the proximal direction with respect to the needle retainer.

10. A drug delivery device according to claim 9, comprising engagement means configured to engage with the needle assembly.

11. A drug delivery device according to claim 10, wherein the bung is retractable to the proximal direction with respect to the needle retainer, the bung comprising the engagement means.

12. A drug delivery device according to claim 10, wherein the needle comprises mating means configured to engage with the engagement means.

13. A drug delivery device according to claim 10, wherein the engagement means are formed as a cavity and wherein the mating means are formed as a needle mount located at the proximal end of the needle.

14. A drug delivery device, comprising a seal member being configured to seal a chamber of the drug delivery device which is suitable to contain a drug, wherein the seal member comprises a diaphragm, and wherein the drug delivery device further comprises a bung and a needle assembly having a needle with a distal end and a proximal end and a needle holder mounted to the needle, the needle holder being moveable in the distal direction with respect to a housing of the drug delivery device so that the needle moves from a first position, where the needle is positioned inside the housing, to a second position, where the needle is extended from the housing, and wherein the seal member is configured to engage with the needle holder.

15. A drug delivery device according to claim 14, wherein the seal member is configured to move in the distal direction with respect to the housing from a first position to a second position when the bung moves in the distal direction with respect to the housing.

16. A drug delivery device according to claim 14, wherein the seal member is moved in the proximal direction with respect to the housing when the needle is retracted in the housing.

\* \* \* \* \*

UNITED STATES PATENT AND TRADEMARK OFFICE
CERTIFICATE OF CORRECTION

PATENT NO. : 8,597,256 B2  Page 1 of 1
APPLICATION NO. : 13/202439
DATED : December 3, 2013
INVENTOR(S) : Lanin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this
Twenty-second Day of September, 2015

Michelle K. Lee
*Director of the United States Patent and Trademark Office*